US006361550B2

(12) United States Patent
Grey et al.

(10) Patent No.: US 6,361,550 B2
(45) Date of Patent: Mar. 26, 2002

(54) AUTOMATICALLY MODULATING ACUPRESSURE DEVICE

(75) Inventors: Thomas L. Grey, San Marcos; Robert J. Duffy, Poway, both of CA (US)

(73) Assignee: Woodside Biomedical, Inc., Carlsbad, CA (US)

( * ) Notice: Subject to any disclaimer, the term of this patent is extended or adjusted under 35 U.S.C. 154(b) by 0 days.

(21) Appl. No.: 09/843,436

(22) Filed: Apr. 26, 2001

Related U.S. Application Data

(63) Continuation of application No. 09/489,665, filed on Jan. 19, 2000, now Pat. No. 6,228,103.

(51) Int. Cl.[7] ................................................ A61B 17/00

(52) U.S. Cl. ....................................... 606/204; 601/107

(58) Field of Search ............................ 606/1, 201, 203, 606/204, 204.15, 204.25; 601/107, 108

(56) References Cited

U.S. PATENT DOCUMENTS

| | | | | | |
|---|---|---|---|---|---|
| 4,069,816 | A | * | 1/1978 | Yamamura et al. | |
| D274,557 | S | | 7/1984 | Griffith | D24/99 |
| 4,574,787 | A | | 3/1986 | Jacobs | 128/64 |
| 4,632,095 | A | * | 12/1986 | Libin | |
| 4,981,146 | A | | 1/1991 | Bertolucci | 128/802 |
| 5,078,728 | A | | 1/1992 | Giarratano | 606/204 |
| 5,224,429 | A | * | 7/1993 | Mocny | |
| 5,269,767 | A | | 12/1993 | Wilk et al. | 606/204.15 |
| D356,433 | S | | 3/1995 | Humphrey | D2/614 |
| 5,601,598 | A | | 2/1997 | Fisher | 606/204 |
| 5,607,749 | A | | 3/1997 | Strumor | 428/156 |
| 5,695,520 | A | | 12/1997 | Bruckner | 606/204 |
| 5,709,647 | A | | 1/1998 | Ferber | 601/134 |
| 5,774,424 | A | | 6/1998 | Yoo | 368/10 |
| 5,951,501 | A | * | 9/1999 | Griner | 601/108 |
| 6,027,521 | A | | 2/2000 | Ourada | 606/204 |
| 6,228,103 | B1 | * | 5/2001 | Grey et al. | 606/204 |

* cited by examiner

*Primary Examiner*—Henry J. Recla
*Assistant Examiner*—William W Lewis
(74) *Attorney, Agent, or Firm*—K. David Crockett, Esq.; Crockett & Crockett

(57) ABSTRACT

An acupressure device with mechanisms for modulating the pressure applied to the user.

5 Claims, 4 Drawing Sheets

AUTOMATICALLY MODULATING ACUPRESSURE DEVICE

RELATED PATENTS

This is a continuation of application Ser. No. 09/489,665, filed Jan. 19, 2000, now U.S. Pat. No. 6,228,103.

FIELD OF THE INVENTIONS

The present invention relates generally to the field of acupressure.

BACKGROUND OF THE INVENTIONS

Stimulation of various areas on the body is known to be an effective treatment method for various conditions that affect the body. These areas lie along certain channels or meridians according to the practice of acupuncture and are typically of small size, often referred to as acupuncture points on the body. Treatment typically consists of stimulation of a certain combination of these areas in a single therapeutic session. The combination and sequence of stimulation has been determined through thousands of years of acupuncture experimentation.

Stimulation can be done invasively using small needles that are manipulated once inserted into an acupuncture area (acupuncture), by applying electrical pulses to the invasive needles (electroacupuncture), or by applying a heated element to the invasive needles (moxibustion). For example, Bertolucci, *Nausea Control Device*, U.S. Pat. No. 4,981,146 (Jan. 1, 1991) describes a nausea control device in the form of a watch-like housing attachable to the human wrist by an adjustable attachment band. The device uses non-invasive nerve stimulation whereby electricity is passed through two electrodes to stimulate nerves located on the ventral side of the wrist (this anatomical position is sometimes referred to as the palmar side of the wrist). The treatment provided by the device is sometimes referred to as electro-acupuncture, which is a form of acupuncture. The ventral site of application is referred to in the acupuncture art as the P6 point, pericardium 6 point, or master point of the pericardium meridian (sometimes referred to as the vascular meridian).

Another method is to use noninvasive, localized pressure applied to the acupuncture area using a fingertip or a small, hard, typically rounded instrument (acupressure). Portable devices for acupressure stimulation of an acupuncture area have been proposed and some are available for use by the lay person. For example, the Sea-Band (Sea-Band UK Ltd., USA) acupressure device is used for treating nausea due to motion sickness and is comprised of an elastic band with an incorporated hard, plastic nodule that is placed over the P6 area. Similar devices with elastic or inelastic bands have been proposed for treating nausea and vomiting by stimulating acupuncture areas on the wrist, e.g., Giarratano, U.S. Pat. No. 5,078,728, Humphrey, U.S. Pat. No. D356,433, Bruckner et al., U.S. Pat. No. 5,695,520, Griffith, U.S. Pat. No. D274,557, Ferber, U.S. Pat. No. 5,709,647. Yoo (U.S. Pat. No. 5,774,424) describes an acupressure stimulator consisting of a pressure plate with nodules. The plate is attached to the back of a watch for stimulating the wrist area.

The acupressure methods described above deliver a constant level of pressure to the acupuncture site to be stimulated. The scientific literature indicates that this type of constant acupressure can be effective, but that the effect is not consistent and typically wanes over time. This is because of the well-known nerve response referred to as nerve accommodation, wherein the nerve accommodates to a constant stimulus and essentially ignores it. The action potentials necessary to achieve the effect are then no longer produced. Thus, the user may receive short-term benefit that wanes with time causing the undesirable symptoms to reappear.

Attempts have been made to circumvent this defect in constant pressure acupressure devices. Jacobs (U.S. Pat. No. 4,574,787) describes a liquid filled device wherein the fluid is caused to vibrate, the vibration causing a changing pressure. A separate vibration source is necessary and the liquid may leak. Strumor (U.S. Pat. No. 5,607,749) describes a similar system in which air is used as the fluid and movement causes differential pressure leading to air flow into certain protuberances causing them to exert variable pressure; movement is necessary to achieve the changing pressure so the user cannot be stationary. Fisher (U.S. Pat. No. 5,601,598) describes a method in which the user is required to periodically stretch a band to cause changing pressure. This requires the user to stop any activity to stretch the band. While these methods have some functionality, they suffer from needing bulky equipment or active user participation that severely limits their utility. Typical users of the anti-nausea wrist mounted acupressure range from sailors who might suffer motion sickness but require unhindered mobility to sedentary and ill patients desiring peaceful rest. These patients require extended periods of treatment, and the current devices are inconvenient and unworkable because they require constant operator action or immobility. For patients desiring extended treatment to be applied during normal activities and during rest, without operator attention, the devices described below are desired.

SUMMARY

The device of the present invention is designed to automatically modulate the pressure provided by an acupressure device over a predetermined period. In the preferred embodiment, a small DC motor is used to rotate a cam across an acupressure nodule. The rotational speed of the motor is such that one revolution is achieved every 3 to 5 seconds as recommended in the scientific literature to avoid nerve accommodation. The motor is battery powered and is fully automatic once it is turned on by the user. In one method of use, the devices are worn on the wrist and energized to provide acupressure on the P6 acupuncture point to provide treatment for nausea and vomiting. The device may be used on other acupuncture points as well.

DETAILED DESCRIPTION OF THE INVENTIONS

Figure 1:
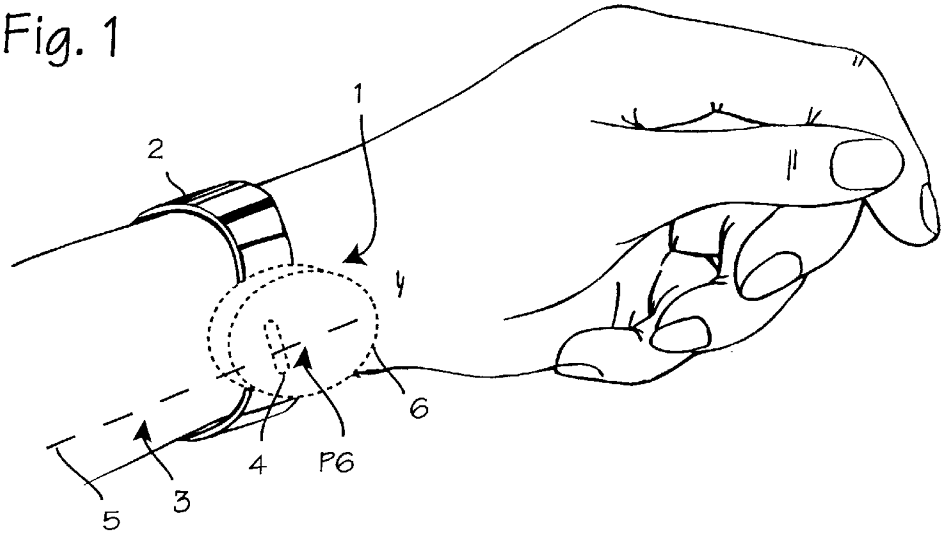
FIG. 1 is an overview of the application of the device on the P6 acupuncture point of a patient.

FIG. 1 illustrates a use of the automatically modulating acupressure device in stimulation of the P6 or Neiguan point on the underside of the wrist to alleviate nausea and vomiting. The wristwatch-like device is worn on the wrist and energized to provide physical stimulation to the wrists. The acupressure device 1 is secured with strap 2 to the ventral side of the wrist 3 such that a protruding nodule 4 is disposed over the median nerve 5 (indicated by the phantom line) and in contact with the skin in the vicinity of the P6 acupuncture point. The nodule is on the underside of the housing or casing 6, and the required power source (a battery or watch spring), operating mechanism and controller are housed within the housing. When placed on the wrist as illustrated, the nodule will stimulate the median nerve and collateral or associated nerve structures and the P6 or Neiguan acupuncture point. Where the device is battery powered, the control means may include an electronic circuit and the operating mechanism may be any number of electromechanical devices capable of creating the required movement of the nodule. Where the device is spring powered, the controller and operating mechanism may be the watch-like gear assembly with gearing selected to achieve the desired periodicity of movement of the nodule. Any required operator controls or input mechanisms are located on the outer face of the housing. The strap may be elastic or inelastic, and may secured by buckling around the wrist, or may secured with adhesives to the wrist.

Figure 2:
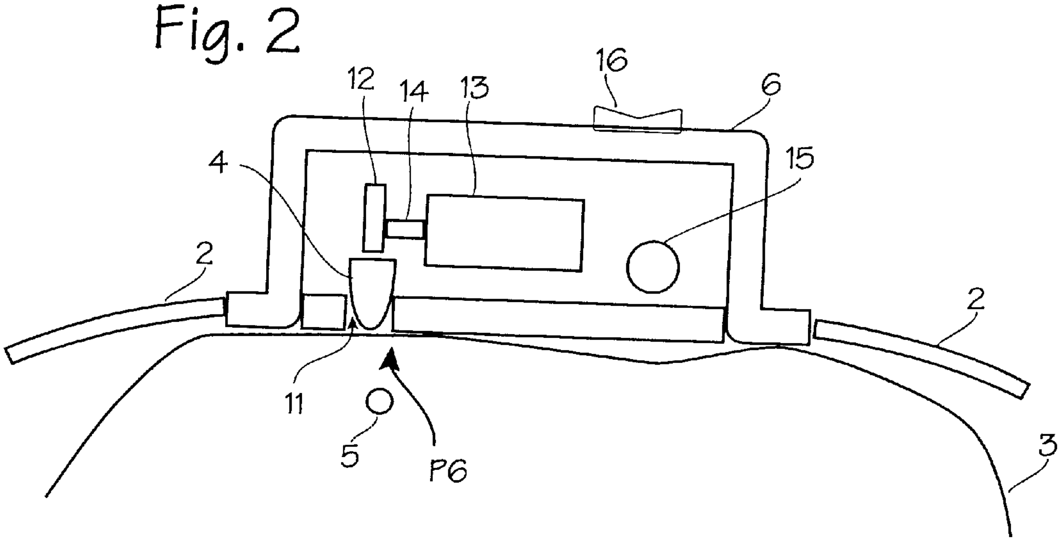
FIG. 2 illustrates an embodiment of acupressure device in which acupressure is applied by a nodule which is driven by a cam to provide modulation in the pressure applied by the nodule.
Figure 3:
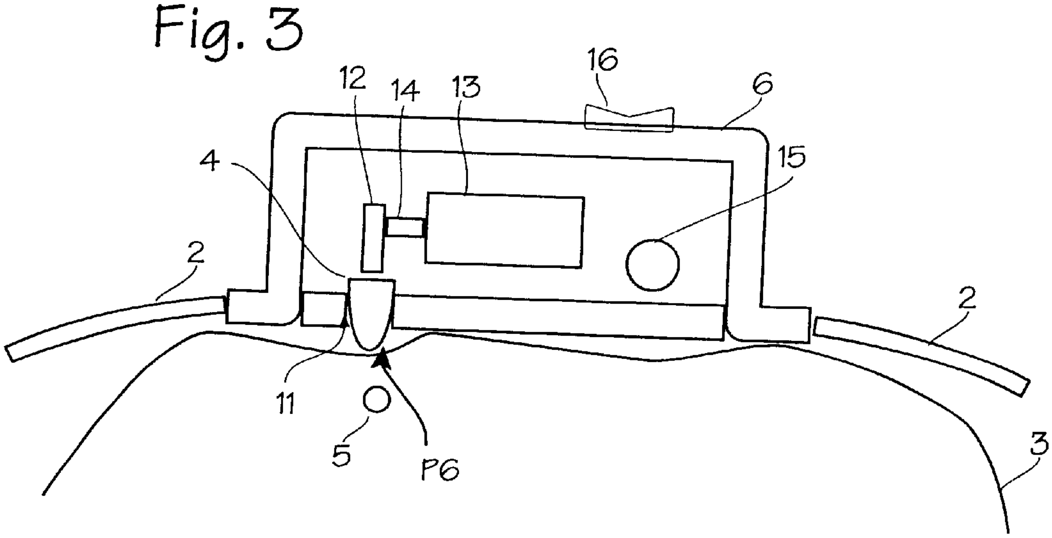
FIG. 3 illustrates the device of FIG. 2 with the cam rotated to provide differential applied pressure.

FIG. 2 is a cross section of the device designed for applying automatically modulated acupressure to the P6 or Neiguan point on the underside of the wrist for controlling nausea and vomiting. The device includes the housing 6 with an underside or bottom 10 which in use will be oriented toward the body and a top which will be oriented away from the body. The housing is secured to the wrist with the strap 2 which may be attached to the housing in any suitable manner. The nodule 4 is located within the aperture 11 in the housing bottom, and protrudes to varying extent from the housing bottom through the aperture. The device is placed on the wrist 3 such that aperture 11 overlies the P6 point and the median nerve 5. The nodule is driven downward through the aperture by a reciprocating mechanism comprising a cam wheel 12, which is driven by a motor 13 or other drive means through the rotating shaft 14. A power supply battery 15 provides power for the motor. A user operated selector 16 is located on the exterior of the housing and is operably connected to the battery and motor so allow user control of the motor. The cam, motor, shaft and power supply are all located within the housing. The nodule is a small round or irregularly shaped mass, and may be comprised of metal, plastic, rubber or other material and may be hard or soft, and may be made in various shapes adapted to slidably move through the aperture. The cam wheel may be any wheel or disk with a radially extending protrusion, or any wheel that rotates about an axis other than its radial center, or any rotating element that is not circular, such as an ellipse. As shown in FIG. 3, rotation of the cam wheel so that the protuberance of the cam wheel is turned into alignment with the nodule forces the nodule outwardly from the housing, through the aperture and toward the user's skin.

In use, the device is placed on the on the body with the nodule in apposition to the acupuncture point to be stimulated. To provide acupressure relief from nausea and vomiting, the device is placed on the inside of the wrist with the bottom 10 facing the wrist so that the aperture and nodule are placed over the P6 point. The strap is then tightened enough to keep the nodule in place. The user operates the control switch to initiate modulation. The motor slowly rotates the cam wheel and the motor shaft. When the short radius of the cam wheel is over the nodule, the nodule is forced upwardly into the housing by the natural resiliency of the user's skin and assumes the position illustrated in FIG. 2. In this position, the small radius portion of the cam wheel may be completely within the aperture, or may protrude from the aperture to a lesser extent than the long radius portion so that is provides pressure against the user's body to a lesser extent than it does when rotated to place the long axis portion in apposition to the skin. When the long radius of the disk is over the nodule, the nodule is maximally displaced into the users skin (FIG. 3). As the as the cam wheel is rotated by the motor, the pressure provided by the nodule into the skin is automatically decreased and increased. The nodule acts as a follower for the cam, and the reciprocating mechanism of the cam wheel may positively engage the nodule so that both upward and downward movement of the nodule is driven by the cam.

Figure 4:
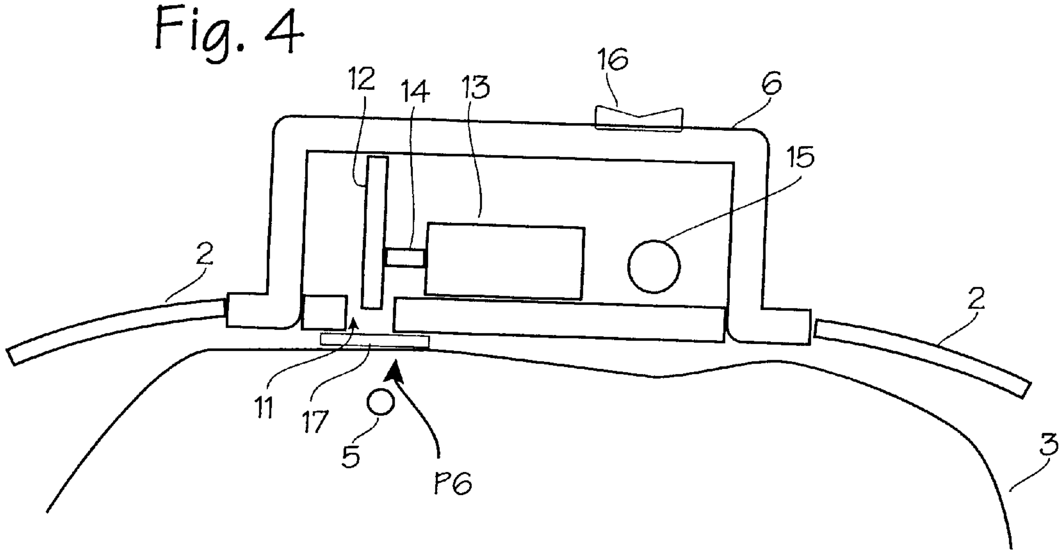
FIG. 4 illustrates an embodiment of this apparatus in which the modulation of acupressure is provided directly by a cam.
Figure 5:
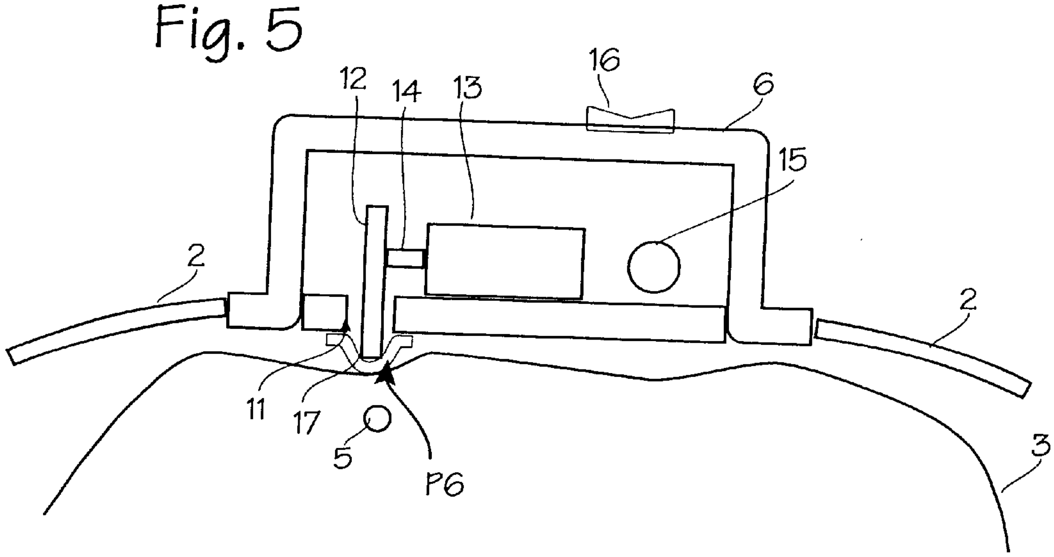
FIG. 5 illustrates the device of FIG. 4 with the cam rotated to provide differential applied pressure.
Figure 6:
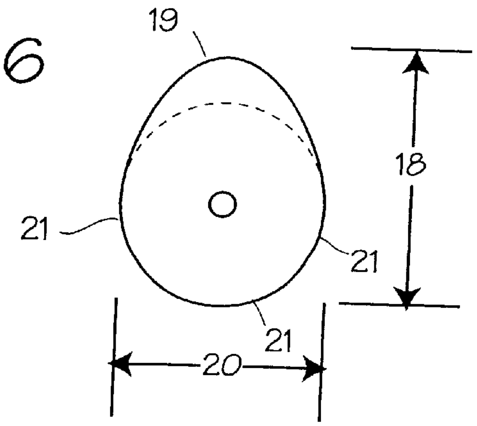
FIG. 6 shows the cam used in the device of FIG. 4.

FIG. 4 illustrates a second embodiment of this apparatus in which the modulation of acupressure is provided directly by a cam wheel. The device includes the housing, 6 with the bottom 10 having an aperture 11, a cam wheel 12 operated by the motor 13 through the shaft 14, powered by the battery 15. In this embodiment, the cam wheel includes one or more protuberances which are sized and dimensioned to protrude from the aperture 11. The aperture is covered with a resilient and flexible sheet 17. As the cam wheel turns, the protuberance is brought into alignment with the aperture and extends outwardly from the aperture and into contact with the user. The flexible sheet covers a hole in the base of the device and allows it to be sealed against water, dust, etc. When the short radius 20 of the disk is over the flexible sheet, the flexible sheet merely rests against the skin (FIG. 4). When the long radius of the disk 18 (see FIG. 6) is over the flexible sheet, the narrow end of the disk protrudes through the hole 11, causing the flexible sheet to press into the user's skin, as shown in FIG. 5. The shape of the disk is illustrated in FIG. 6. The disk is shaped in a profile similar to an egg wherein the long radius 18 corresponds to the narrow end of the disk and defines a cam or protuberance 19 and a short radius 20 which defines a relatively non-protruding arc 21 around the disk. This cam wheel can be replaced with any other form of cam and follower arrangement, such as a downwardly facing cam disk with a protrusion extending downwardly from an arcuate portion of the disk. The cam disk and its protrusion may act on a nodule, or they may act on a flexible sheet, to provide variable pressure to the acupuncture point.

Through slow rotation of the disk, the embodiments in FIGS. 2 and 4 can achieve a continuous modulation, for example, achieving a sinusoidal modulation of the pressure applied to the acupressure point. The speed of rotation of the cam wheel may be varied to accommodate the user, and controls may be provided to adjust the speed of the rotation within therapeutic ranges of 3 to 5 seconds per rotation.

Figure 7:
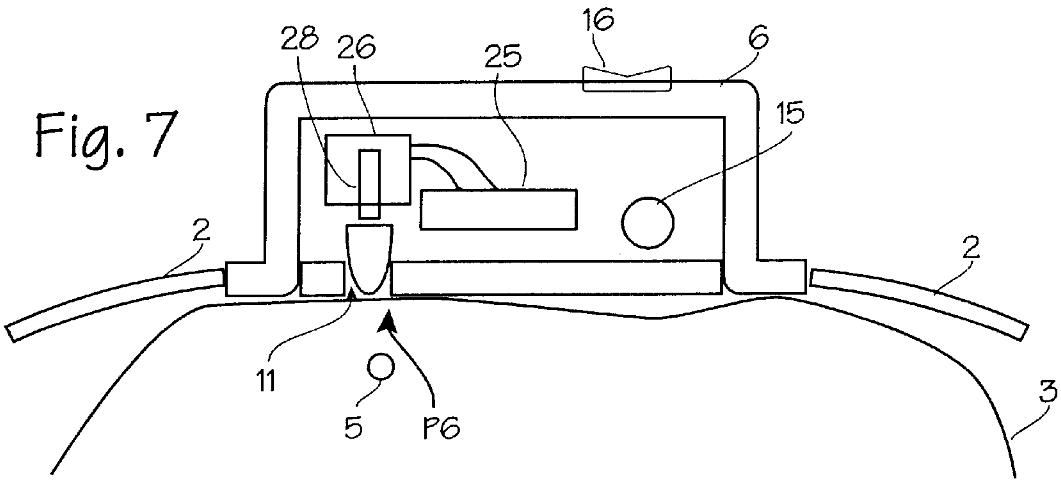
FIG. 7 illustrates an embodiment of the acupressure device in which the modulation of acupressure is provided by a solenoid acting on a nodule.
Figure 8:
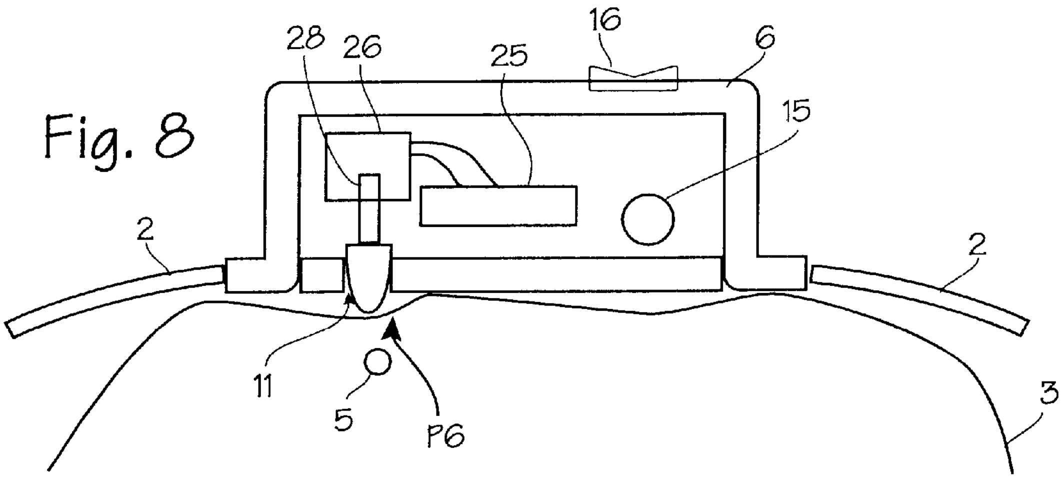
FIG. 8 illustrates the device of FIG. 7 with the solenoid is driven outwardly to provide differential applied pressure.
Figure 9:
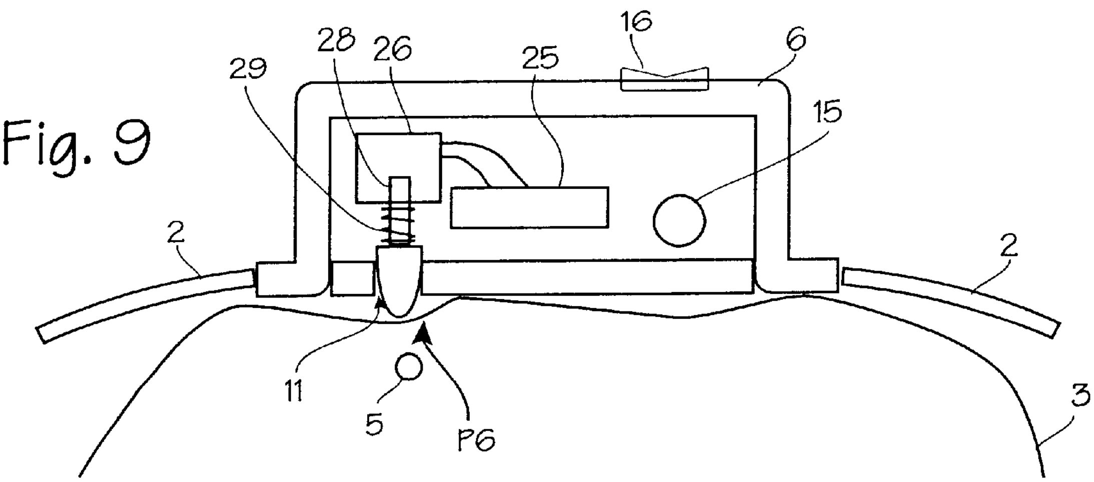
FIG. 9 illustrates the device of FIG. 7 modified with the addition of a biasing spring.

Other automatically modulating devices can be implemented to achieve the same function. For example, a miniature solenoid can be used to drive the nodule against the skin directly in vertical direction as shown in FIGS. 7 and 8. In this embodiment, the device includes the housing, 6 with the bottom 10 having an aperture 11 with the nodule 4 protruding through the aperture. A solenoid 26 powered by the battery 15 operates to drive the nodule upwardly or downwardly within the aperture. A controller 27 is programmed to operate the solenoid to move the nodule through the aperture. As illustrated in FIG. 8, when energized, the solenoid drives its core 28 in to the nodule, thereby driving the nodule downwardly through the aperture and into the patient's skin. The nodule is biased upwardly by the natural resilience of the user's body. Alternatively, as illustrated in FIG. 9, the nodule may be biased downwardly with spring 29 to hold the nodule against the skin, and the solenoid may be occasionally operated to lift the nodule away from the skin. Depending on the periodicity and pressure profile desired, battery usage may be minimized in this embodiment. The periodicity of lifting or driving the solenoid may be varied within the same parameters as the rotation of the cam wheel discussed above.

Figure 10:
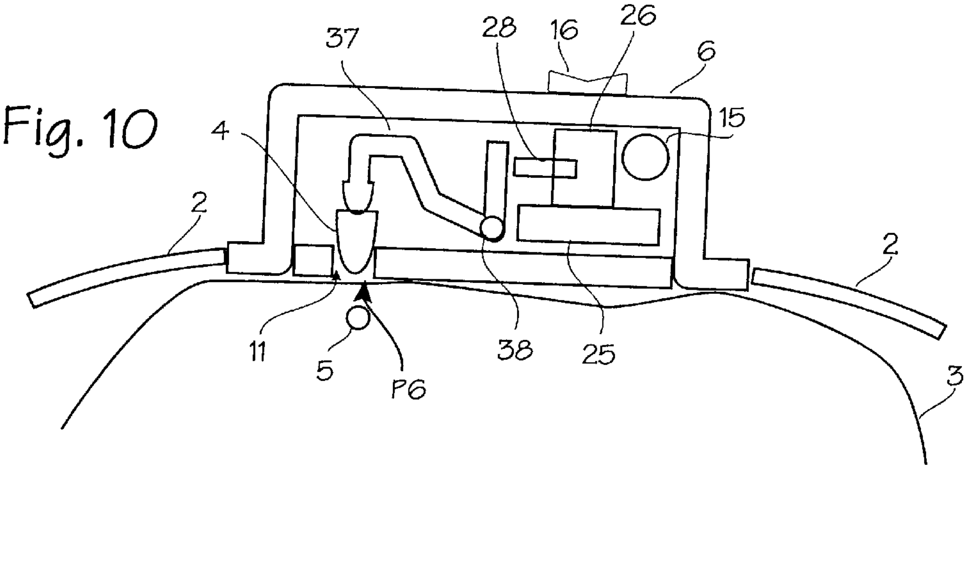
FIG. 10 illustrates an embodiment of the acupressure device in which the modulation of acupressure is provided by a pivoted linkage acting on a protruding nodule.

In still another embodiment, a solenoid can drive the nodule through a simple lever arrangement as shown in FIG. 10. In this embodiment, the housing 6 with the bottom 10 and aperture 11 with the nodule 4 protruding through the aperture are similar to the previous embodiments. The solenoid 26 is oriented horizontally relative to the bottom of the housing, and movement of the solenoid core 28 operates lever 37, rotating the lever about pivot 38. This translates horizontal movement of the solenoid into a vertical movement the nodule. The nodule can be replaced either directly by the end of the solenoid in FIG. 7 or by the end of the lever in FIG. 10, and can also be covered by the flexible sheet seal shown in FIG. 4.

Each embodiment may use a watch-like mechanism of gears to drive a cam or lever mechanism against the nodule. Such a watch-like mechanism of gears can be battery powered or powered through a wind-up spring as in a traditional watch. In addition, recent advances in micromachining can produce very small gear arrangements utilizing micro-electro-mechanical systems or MEMS technology. With appropriate gear design, a MEMS approach can be used to achieve a very small implementation of the traditional watch mechanism of gears to produce the desired modulation in a very low profile device.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for providing variable pressure to a point on the wrist of a person, said device comprising:

a housing comprising a bottom portion and a top portion, said bottom portion adapted be placed in apposition to the point on the wrist and to rest on the body in proximity to the point on the wrist, said bottom portion having an aperture positioned so as to overlie the point when the bottom is placed in apposition to the point;

a strap for attaching the housing to the wrist of a person, said strap adapted to be secured on the body and hold the housing to the body;

a nodule disposed within the housing, said nodule adapted to slide inwardly and outwardly from the housing through the aperture, said nodule sized and dimensioned to impinge upon an acupuncture point on the wrist without substantially impinging on adjacent areas of the wrist;

a reciprocating mechanism disposed within the housing, said reciprocating mechanism operably connected to the nodule such that reciprocating action of the reciprocating mechanism tends to cause outward movement of the nodule through the aperture.

2. The device of claim 1 wherein the nodule has a maximum lateral cross section relative to the wrist of about 1 cm.

3. The device of claim 1 wherein the reciprocating mechanism comprises:

a cam wheel operably engaging the nodule;

a motor disposed within the housing and operably connected to the cam wheel for rotating the cam wheel.

4. The device of claim 1 wherein the reciprocating mechanism comprises:

a solenoid operably engaging the nodule;

a power supply within the housing, said power operably connected to the solenoid;

a controller within the housing, said controller programmed to operate the solenoid to move the nodule through the aperture.

5. The device of claim 1 wherein the reciprocating mechanism comprises:

a linkage operably engaging the nodule to urge the nodule through the aperture;

a solenoid operably engaging the linkage;

a power supply within the housing, said power operably connected to the solenoid;

a controller within the housing, said controller programmed to operate the solenoid to actuate the linkage.

* * * * *